US011478175B1

(12) United States Patent
Diju et al.

(10) Patent No.: US 11,478,175 B1
(45) Date of Patent: Oct. 25, 2022

(54) DEVICES FOR COLLECTING CAPILLARY BLOOD AND METHODS FOR SAME

(71) Applicant: Paulus Holdings Limited, Dublin (IE)

(72) Inventors: Taufeeq Elahi Diju, Dublin (IE); Kathleen Gahan, Gorey (IE); Ronan P. Ryan, Dublin (IE)

(73) Assignee: Paulus Holdings Limited, Dun Laoghaire (IE)

( * ) Notice: Subject to any disclaimer, the term of this patent is extended or adjusted under 35 U.S.C. 154(b) by 0 days.

(21) Appl. No.: 17/591,342

(22) Filed: Feb. 2, 2022

Related U.S. Application Data

(60) Provisional application No. 63/257,630, filed on Oct. 20, 2021.

(51) Int. Cl.
  *A61B 5/15* (2006.01)
  *A61B 5/151* (2006.01)

(52) U.S. Cl.
  CPC .... *A61B 5/150099* (2013.01); *A61B 5/15117* (2013.01); *A61B 5/150221* (2013.01); *A61B 5/150236* (2013.01); *A61B 5/150267* (2013.01); *A61B 5/150297* (2013.01); *A61B 5/150343* (2013.01)

(58) Field of Classification Search
  CPC ........ A61B 5/150007–150992; A61B 5/15117
  See application file for complete search history.

(56) References Cited

U.S. PATENT DOCUMENTS

| | | |
|---|---|---|
| 8,561,795 B2 | 10/2013 | Schott |
| 8,808,202 B2 | 8/2014 | Brancazio |
| 8,821,412 B2 | 9/2014 | Gonzalez-Zugasti et al. |
| 8,827,971 B2 | 9/2014 | Gonzalez-Zugasti et al. |
| 9,033,898 B2 | 5/2015 | Chickering, III et al. |
| 9,041,541 B2 | 5/2015 | Levinson et al. |
| 9,113,836 B2 | 8/2015 | Bernstein et al. |
| 9,119,578 B2 | 9/2015 | Haghgooie et al. |
| 9,289,763 B2 | 3/2016 | Berthier et al. |
| 9,295,417 B2 | 3/2016 | Haghgooie et al. |
| 9,730,624 B2 | 8/2017 | Gonzalez-Zugasti et al. |
| 9,775,551 B2 | 10/2017 | Bernstein et al. |

(Continued)

FOREIGN PATENT DOCUMENTS

| | | | |
|---|---|---|---|
| AU | 2012249683 A1 | 11/2013 | |
| AU | 2012249692 A1 | 11/2013 | |

(Continued)

*Primary Examiner* — David J. McCrosky
(74) *Attorney, Agent, or Firm* — Goodwin Procter LLP

(57) ABSTRACT

A device for collecting blood from a mammalian subject without using spontaneous capillary blood flow, the device including a collection cup subassembly having a cantilevered, concave slide for transporting blood down and away from a blood sampling location; a mid-body subassembly couplable to the collection cup assembly and including a housing having a proximal end and a distal end and defining a plenum space; and a plunger subassembly having a first end and a second end and including a plunger formed at the second end and one or more lancet elements attached to the plunger. Advantageously, the plunger and lancet elements are structured and arranged to translate through the mid-body subassembly and the collection cup subassembly to the blood sampling location.

26 Claims, 4 Drawing Sheets

(56) References Cited

U.S. PATENT DOCUMENTS

| | | |
|---|---|---|
| 9,987,629 B2 | 6/2018 | Berthier et al. |
| 10,188,335 B2 | 1/2019 | Haghgooie et al. |
| 10,426,390 B2 | 10/2019 | Berthier et al. |
| 10,492,716 B2 | 12/2019 | Berthier et al. |
| 10,543,310 B2 | 1/2020 | Bernstein et al. |
| 10,638,963 B2 * | 5/2020 | Beyerlein ........ A61B 5/150251 |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,939,860 B2 | 3/2021 | Levinson et al. |
| 2010/0069726 A1 | 3/2010 | Levinson |
| 2010/0256524 A1 | 10/2010 | Levinson et al. |
| 2010/0269837 A1 | 10/2010 | Levinson et al. |
| 2010/0272652 A1 | 10/2010 | Levinson |
| 2010/0330703 A1 | 12/2010 | Bernstein et al. |
| 2011/0009847 A1 | 1/2011 | Levinson et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0172508 A1 | 7/2011 | Chickering, III et al. |
| 2011/0172510 A1 | 7/2011 | Chickering, III et al. |
| 2011/0251562 A1 | 10/2011 | Chickering, III et al. |
| 2011/0288389 A9 | 11/2011 | Levinson et al. |
| 2012/0016308 A1 | 1/2012 | Schott |
| 2012/0039809 A1 | 2/2012 | Levinson et al. |
| 2012/0041338 A1 | 2/2012 | Chickering, III et al. |
| 2012/0271125 A1 | 10/2012 | Bernstein et al. |
| 2012/0277629 A1 | 11/2012 | Bernstein et al. |
| 2013/0158468 A1 | 6/2013 | Bernstein et al. |
| 2013/0158482 A1 | 6/2013 | Davis et al. |
| 2013/0211289 A1 | 8/2013 | Moga et al. |
| 2014/0186820 A1 | 7/2014 | Queval |
| 2014/0336536 A1 | 11/2014 | Brancazio |
| 2015/0057510 A1 | 2/2015 | Levinson et al. |
| 2015/0087944 A1 | 3/2015 | Levinson et al. |
| 2016/0038068 A1 | 2/2016 | Chickering, III et al. |
| 2017/0120022 A1 | 5/2017 | Chickering, III et al. |
| 2017/0120023 A1 | 5/2017 | Davis et al. |
| 2017/0127991 A1 | 5/2017 | Bernstein et al. |
| 2017/0154164 A9 | 6/2017 | Levinson et al. |
| 2017/0215790 A1 | 8/2017 | Levinson et al. |
| 2017/0224264 A1 | 8/2017 | Brancazio |
| 2018/0008183 A1 | 1/2018 | Chickering, III et al. |
| 2018/0078241 A1 | 3/2018 | Moga et al. |
| 2018/0242890 A1 | 8/2018 | Chickering, III et al. |
| 2019/0015827 A1 | 1/2019 | Berthier et al. |
| 2019/0023473 A1 | 1/2019 | Schott |
| 2019/0053740 A1 | 2/2019 | Bernstein et al. |
| 2019/0159709 A1 | 5/2019 | Barone et al. |
| 2019/0209820 A1 | 7/2019 | Chickering, III et al. |
| 2019/0336058 A1 | 11/2019 | Haghgooie et al. |
| 2020/0015751 A9 | 1/2020 | Chickering, III et al. |
| 2020/0037940 A1 | 2/2020 | Berthier et al. |
| 2020/0085414 A1 | 3/2020 | Berthier et al. |
| 2020/0146606 A1 | 5/2020 | Casavant et al. |
| 2020/0178870 A1 | 6/2020 | Berthier et al. |
| 2020/0323473 A1 | 10/2020 | Berthier et al. |
| 2020/0353155 A1 | 11/2020 | Bernstein et al. |
| 2021/0022681 A1 | 1/2021 | Chickering, III et al. |
| 2021/0059588 A1 | 3/2021 | Welch et al. |

FOREIGN PATENT DOCUMENTS

| | | |
|---|---|---|
| AU | 2013293078 A1 | 2/2015 |
| AU | 2016266112 A1 | 12/2016 |
| AU | 2016269418 A1 | 12/2016 |
| AU | 2015295983 A1 | 2/2017 |
| AU | 2017272264 A1 | 1/2018 |
| AU | 2016377659 A1 | 7/2018 |
| AU | 2018223046 A1 | 9/2018 |
| AU | 2020202814 A1 | 5/2020 |
| BR | 112013027351 A2 | 1/2017 |
| CA | 2833175 A1 | 11/2012 |
| CA | 2833275 A1 | 11/2012 |
| CA | 3009328 A1 | 6/2017 |
| CN | 102405015 A | 4/2012 |
| CN | 102405018 A | 4/2012 |
| CN | 102648015 A | 8/2012 |
| CN | 102791197 A | 11/2012 |
| CN | 102811754 A | 12/2012 |
| CN | 103068308 A | 4/2013 |
| CN | 103370007 A | 10/2013 |
| CN | 103874460 A | 6/2014 |
| CN | 103874461 A | 6/2014 |
| CN | 104434136 A | 3/2015 |
| CN | 106999120 A | 8/2017 |
| CN | 107115115 A | 9/2017 |
| CN | 109068979 A | 12/2018 |
| CN | 109996571 A | 7/2019 |
| CN | 111295138 A | 6/2020 |
| CN | 111657965 A | 9/2020 |
| CN | 112203586 A | 1/2021 |
| EP | 2329035 A2 | 6/2011 |
| EP | 2408369 A1 | 1/2012 |
| EP | 2408372 A1 | 1/2012 |
| EP | 2411055 A2 | 2/2012 |
| EP | 2411067 A1 | 2/2012 |
| EP | 2493535 A2 | 9/2012 |
| EP | 2493536 A2 | 9/2012 |
| EP | 2493537 A2 | 9/2012 |
| EP | 2523603 A2 | 11/2012 |
| EP | 2523706 A2 | 11/2012 |
| EP | 2593014 A1 | 5/2013 |
| EP | 2603256 A2 | 6/2013 |
| EP | 2637562 A1 | 9/2013 |
| EP | 2649507 A1 | 10/2013 |
| EP | 2701598 A1 | 3/2014 |
| EP | 2701600 A1 | 3/2014 |
| EP | 2701601 A1 | 3/2014 |
| EP | 2702406 A1 | 3/2014 |
| EP | 2874942 A1 | 5/2015 |
| EP | 2954916 A2 | 12/2015 |
| EP | 2992827 A1 | 3/2016 |
| EP | 3087919 A1 | 11/2016 |
| EP | 3106092 A2 | 12/2016 |
| EP | 3174463 A1 | 6/2017 |
| EP | 3235429 A1 | 10/2017 |
| EP | 3236259 A1 | 10/2017 |
| EP | 3243435 A1 | 11/2017 |
| EP | 3257442 A2 | 12/2017 |
| EP | 3393342 A1 | 10/2018 |
| EP | 3490453 A1 | 6/2019 |
| EP | 3515521 A1 | 7/2019 |
| EP | 3566649 A1 | 11/2019 |
| EP | 3760106 A2 | 1/2021 |
| EP | 3769682 A1 | 1/2021 |
| JP | 2015062698 A | 4/2015 |
| JP | 05784031 | 9/2015 |
| JP | 05806236 | 11/2015 |
| JP | 2015211878 A | 11/2015 |
| JP | 05826766 | 12/2015 |
| JP | 2016027878 A | 2/2016 |
| JP | 2016039972 A | 3/2016 |
| JP | 06055773 B2 | 12/2016 |
| JP | 06058063 | 1/2017 |
| JP | 06078230 | 2/2017 |
| JP | 06078565 | 2/2017 |
| JP | 2017042641 A | 3/2017 |
| JP | 2017047298 A | 3/2017 |
| JP | 06121400 | 4/2017 |
| JP | 06126783 | 5/2017 |
| JP | 2017121582 A | 7/2017 |
| JP | 2017131697 A | 8/2017 |
| JP | 2017192778 A | 10/2017 |
| JP | 06254545 B2 | 12/2017 |
| JP | 2018011975 A | 1/2018 |
| JP | 06312670 A1 | 4/2018 |
| JP | 2019188182 A | 10/2019 |
| KR | 2013466 | 8/2019 |
| KR | 2237667 | 4/2021 |
| WO | WO-2009149308 A2 | 12/2009 |
| WO | WO-2010101620 A2 | 9/2010 |
| WO | WO-2010101621 A1 | 9/2010 |

(56) References Cited

FOREIGN PATENT DOCUMENTS

| | | |
|---|---|---|
| WO | WO-2010101625 A2 | 9/2010 |
| WO | WO-2010101626 A1 | 9/2010 |
| WO | WO-2010110916 A2 | 9/2010 |
| WO | WO-2010110919 A1 | 9/2010 |
| WO | WO-2010151329 A1 | 12/2010 |
| WO | WO-2011053787 A2 | 5/2011 |
| WO | WO-2011053788 A2 | 5/2011 |
| WO | WO-2011053796 A2 | 5/2011 |
| WO | WO-2011065972 A2 | 6/2011 |
| WO | WO-2011088211 A2 | 7/2011 |
| WO | WO-2011088214 A2 | 7/2011 |
| WO | WO-2011094573 A1 | 8/2011 |
| WO | WO-2011163347 A2 | 12/2011 |
| WO | WO-2012009613 A1 | 1/2012 |
| WO | WO-2012018486 A2 | 2/2012 |
| WO | WO-2012021792 A2 | 2/2012 |
| WO | WO-2012021801 A2 | 2/2012 |
| WO | WO-2012064802 A1 | 5/2012 |
| WO | WO-2012149126 A1 | 11/2012 |
| WO | WO-2012149134 A1 | 11/2012 |
| WO | WO-2012149143 A1 | 11/2012 |
| WO | WO-2012149155 A1 | 11/2012 |
| WO | WO-2012154362 A1 | 11/2012 |
| WO | WO-2013112877 A1 | 8/2013 |
| WO | WO-2014018558 A1 | 1/2014 |
| WO | WO-2015189274 A1 | 12/2015 |
| WO | WO-2016019388 A1 | 2/2016 |
| WO | WO-2016123282 A1 | 8/2016 |
| WO | WO-2017112793 A1 | 6/2017 |
| WO | WO-2018022535 A1 | 2/2018 |
| WO | WO-2018057760 A1 | 3/2018 |
| WO | WO-2019220340 A1 | 11/2019 |
| WO | WO-2020102281 A1 | 5/2020 |
| WO | WO-2020223710 A1 | 11/2020 |
| WO | WO-2021041881 A1 | 3/2021 |
| WO | WO-2021076846 A1 | 4/2021 |

\* cited by examiner

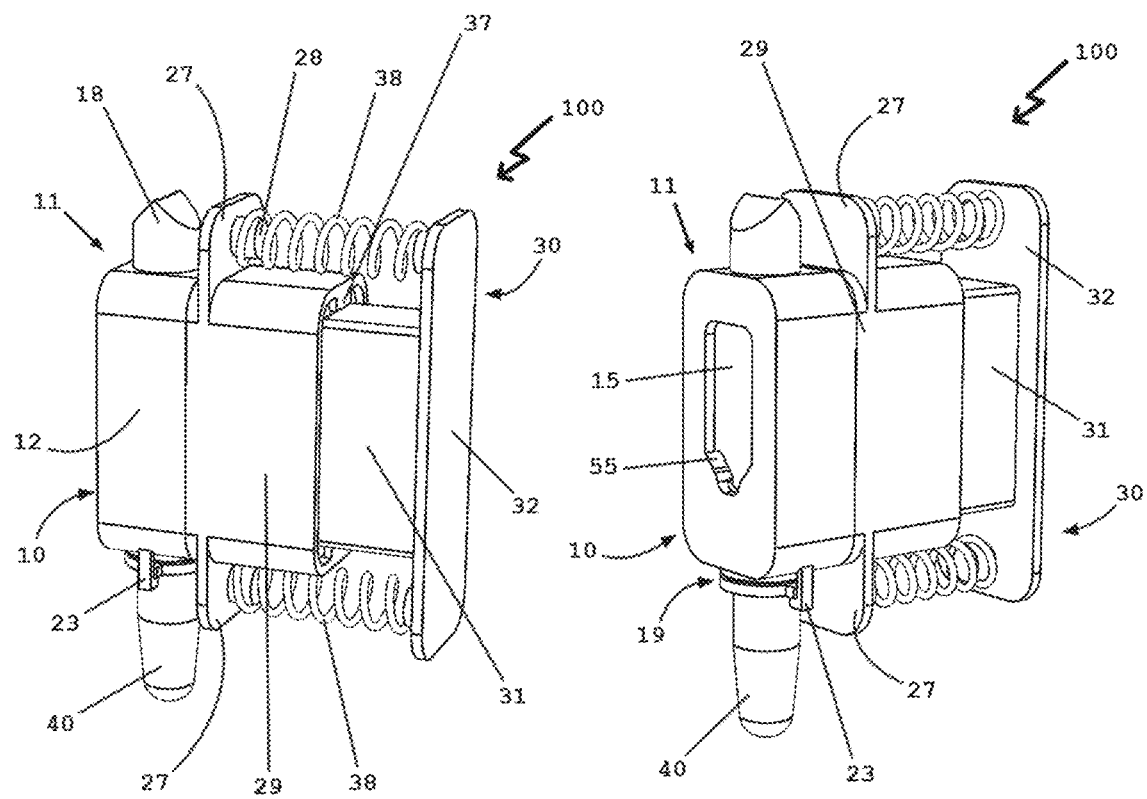
Figure 1
Figure 2
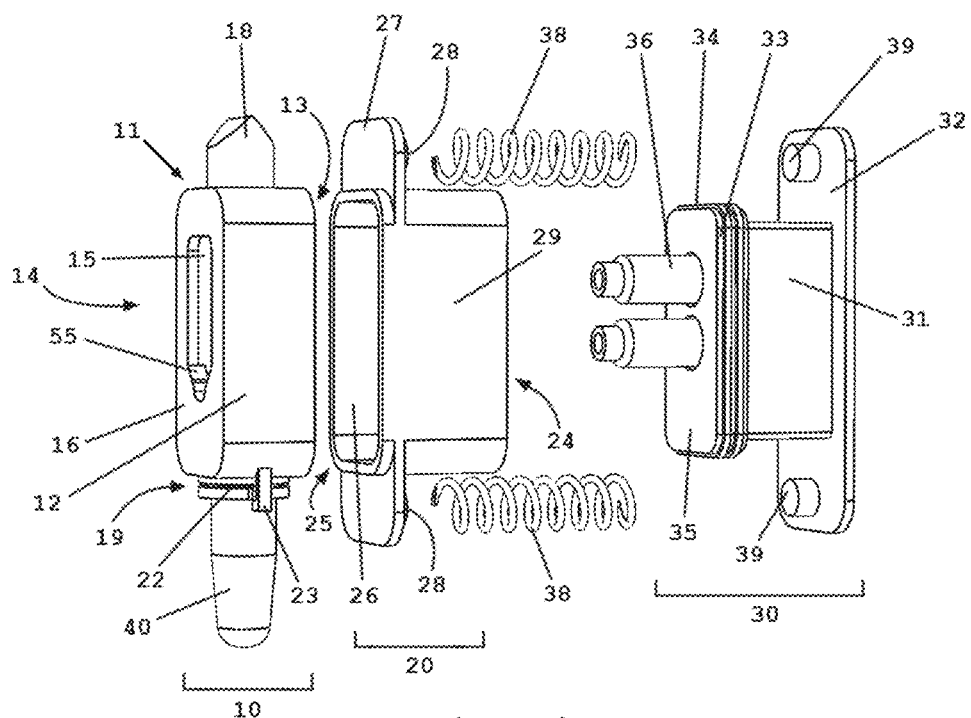
Figure 3

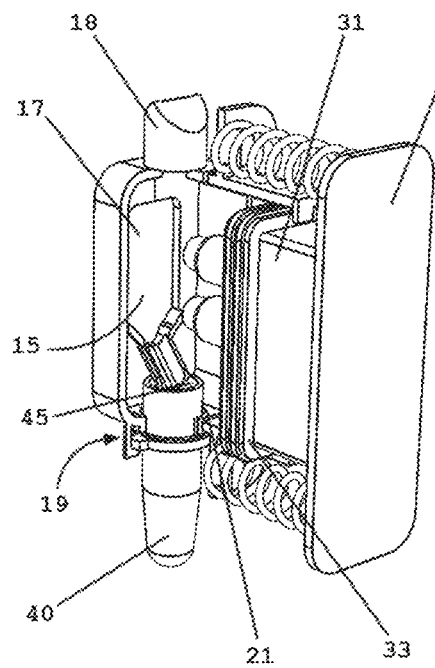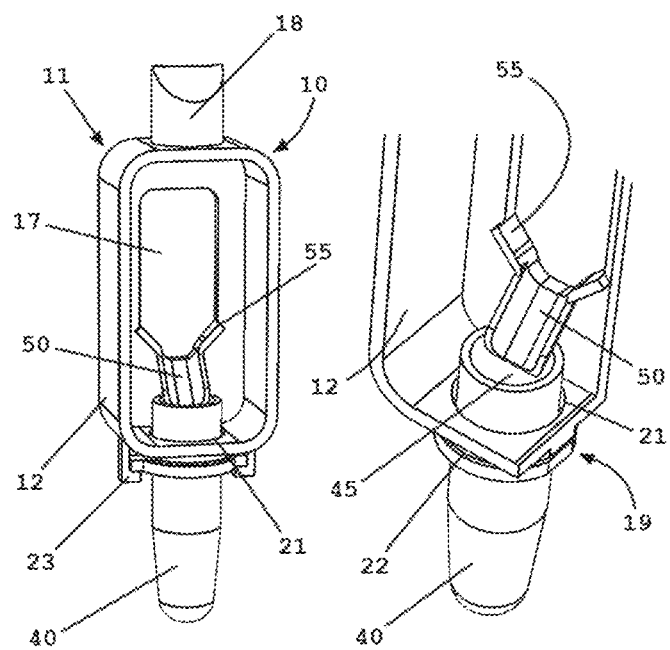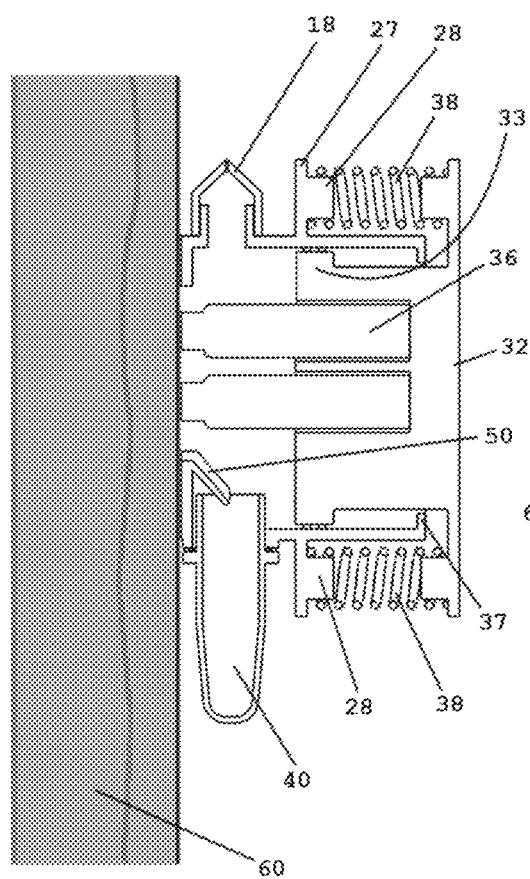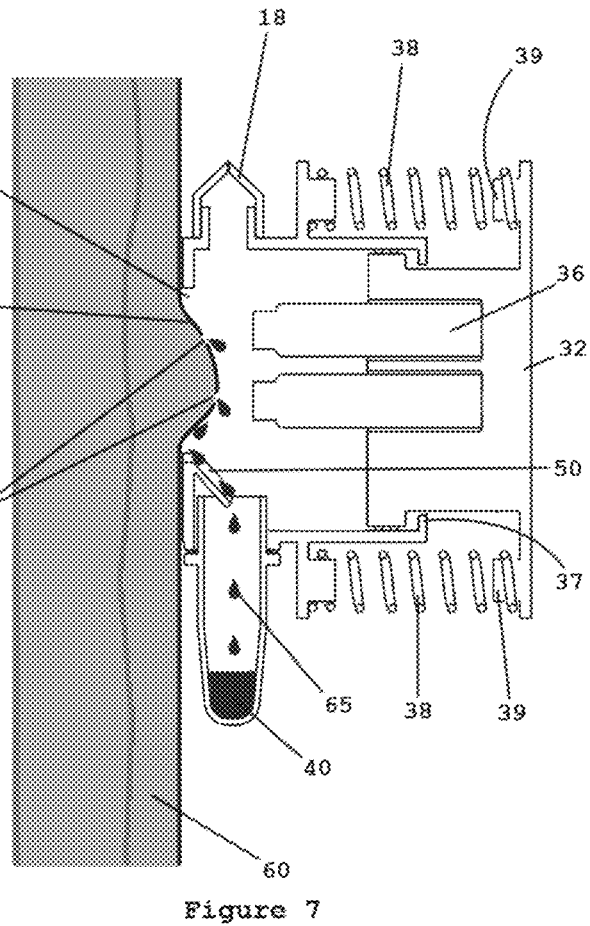
Figure 4     Figure 5A     Figure 5B
Figure 6     Figure 7

DEVICES FOR COLLECTING CAPILLARY BLOOD AND METHODS FOR SAME

CROSS REFERENCE TO RELATED APPLICATION

This application claims priority to U.S. Provisional Patent Application No. 63/257,630 filed on Oct. 20, 2021, the entire contents of which are incorporated herein in their entirety.

FIELD OF THE INVENTION

The present invention relates to devices and methods for collecting capillary blood from a mammalian subject and, more specifically, to blood collecting devices and methods that include a cantilevered slide that slopes down and away from the blood sampling site to draw blood by gravity feed rather than by spontaneous capillary flow.

BACKGROUND OF INVENTION

Conventional blood sampling requires a trained medical professional, e.g., a phlebotomist, who collects blood samples from a mammalian subject, e.g., a human, through venipuncture, for example, using a needle and syringe. Disadvantageously, venipuncture using a needle and syringe is not suitable if the subject prefers to collect a blood sample by herself. Other methods for collecting a blood sample, for example, at the subject's residence, involve collecting capillary blood samples, which do not require a needle, a syringe, venipuncture, or a trained medical professional.

In some applications, capillary blood sample collection includes the use of a lancet and a blood collection tube. More particularly, the lancet may be used to pierce the subject's epidermis, causing blood to rise to the surface of the subject's skin typically from subject's fingertip. Blood is either dripped directly into the blood collection tube, or a capillary tube is employed to transfer blood from the fingertip to the capillary tube. Using either method can sometimes cause spillage of blood. Although such a method and device lend themselves to home use by laypersons who are not trained medical professionals it is a relatively difficult process to drip blood into a vial from the finger.

BRIEF SUMMARY OF THE INVENTION

Accordingly, it would be desirable to provide a device for collecting capillary blood samples that does not suffer from the shortcomings of the prior art. More specifically, the capillary blood samples may be collected at home or at a medical facility by trained medical professionals as well as laypersons. Moreover, by making it easier to collect by a layperson, more samples will be successfully collected.

In a first aspect, the present invention relates to a device for collecting a blood sample. More specifically, in some embodiments, the device includes a collection cup subassembly that has a housing and a cantilevered slide structured and arranged in the housing for transporting blood down and away from a blood sampling location. In some implementations, the slide is cantilevered at an obtuse angle from the opening in the housing in the collection cup subassembly and/or the slide has a shape is selected from the group consisting of a concave slide, a rectangular slide, a rounded rectangular slide, or a V-shaped slide. In some variations, a hydrophobic agent may be applied to the slide.

In some applications, the collection cup subassembly may also include sidewall elements that are formed within and about one or more openings in the housing and that are structured and arranged to funnel blood from the blood sampling location to the slide. In one implementation, the one or more openings include multiple openings. In some variations, the device may also include a blood diverter that is configured to divert blood flow originating in a first opening around a second opening. Preferably, blood flow is diverted along a path that exceeds 2 mm.

Furthermore, the collection cup subassembly may include one or more of the following: a one-way valve disposed in the housing for creating a negative pressure within a plenum space within the housing, an opening formed therethrough for placement against the epidermis of the subject, and/or the housing of the collection cup subassembly may include a connection opening structured and arranged for releasably connecting a blood sample container to the housing of the collection cup subassembly.

In some implementations, the device may also include a mid-body subassembly couplable to the collection cup assembly and comprising a housing having a proximal end and a distal end and defining a plenum space and/or a plunger subassembly having a first end and a second end. In some variations, the mid-body subassembly further includes comprises a pair of opposing tabs formed at the distal end of the housing, wherein the opposing tabs are configured to retain at least one biasing element (e.g., a pair of springs) and/or a tab formed at the proximal end of the housing for retaining a plunger within the plenum space.

In some implementations, the plunger subassembly may include one or more of the following: a first end and a second end with a base portion formed at the first end and a plunger formed at the second end. The base portion may include a pair of protrusions that are structured and arranged to retain a biasing element. At least one lancet element may be attached to the plunger. At least one sealing device may be disposed about the plunger.

In some variations, the plunger and lancet elements are structured and arranged to translate through the collection cup subassembly to the blood sampling location. Advantageously, the plunger may be structured and arranged to create a negative pressure within the collection cup subassembly.

In a second aspect, the present invention relates to a method for collecting a blood sample. More specifically, in some embodiments, the method includes providing a blood collecting device; placing the device at a blood sampling point; applying a force to compress a biasing device, such that the plunger and lancet elements advance towards the blood sampling location; funneling blood down and away from the blood sampling location towards the slide; and collecting blood traveling by a gravity feed via the slide in a blood sample container disposed through an opening in the housing of the collection cup subassembly. In some applications, the device includes a collection cup subassembly having a cantilevered slide for transporting blood down and away from a blood sampling location; a mid-body subassembly couplable to the collection cup assembly and comprising a housing having a proximal end and a distal end and defining a plenum space; and a plunger subassembly having a first end and a second end. In some variations, a plunger may be formed at the second end and at least one lancet element maybe attached to the plunger.

In some implementations, the slide may be cantilevered at an obtuse angle from the opening in the housing in the collection cup subassembly and/or compressing the biasing device causes air within the device to be expelled, creating a negative pressure within the device. For example, the negative pressure may be created by expelling air via a one-way valve.

DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1 shows a bottom perspective view of a device for collecting blood samples, in accordance with some embodiments of the present invention;

FIG. 2 shows a top perspective view of the device of FIG. 1, in accordance with some embodiments of the present invention;

FIG. 3 shows an exploded view of a top perspective view of the device of FIG. 1, in accordance with some embodiments of the present invention;

FIG. 4 shows a bottom perspective view of the device of FIG. 1 with a portion of the mid-body subassembly removed, in accordance with some embodiments of the present invention;

FIG. 5A shows a bottom perspective view of the collection cup subassembly of the device of FIG. 1, in accordance with some embodiments of the present invention;

FIG. 5B shows a detail of the collection cup subassembly of the device of FIG. 5A, in accordance with some embodiments of the present invention;

FIG. 6 shows a cross-sectional side (elevation) view of the device of FIG. 1 with the lancets advanced towards the subject's epidermis, in accordance with some embodiments of the present invention;

FIG. 7 shows a cross-sectional side (elevation) view of the device of FIG. 6 with the lancets retracted, in accordance with some embodiments of the present invention;

DETAILED DESCRIPTION

Figure 9:
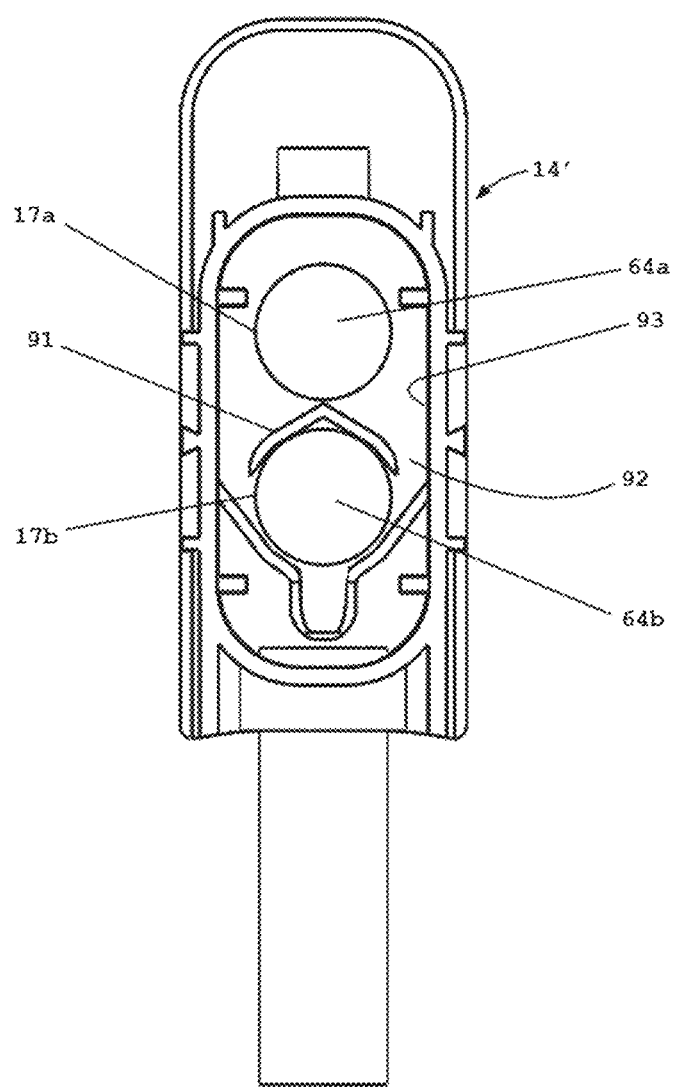
FIG. 9 shows a collection cup subassembly having a plurality of smaller openings, in accordance with some embodiments of the present invention.

Referring to FIGS. 1-4, an illustrative embodiment of a device for collecting a blood sample from a mammalian subject is shown. Advantageously, the device 100 is structured and arranged so that blood is not collected using spontaneous capillary flow. In some implementations, the device 100 consists or consists essentially of a collection (or suction) cup subassembly 10, as well as two other subassemblies: a mid-body subassembly 20, and a plunger subassembly 30. In some applications, the (e.g., elongate, rectangular or rounded rectangular) collection cup subassembly 10 may include a (e.g., plastic) suction cup 11 having a housing 12 that is formed to provide an open, proximal end 13; a partially open, distal end 14; and a plenum space 15. In some variations, the distal end 14 includes an (e.g., planar, concave, convex, and so forth) upper surface 16 having an opening 17 formed therein to provide access to the plenum space 15. Although the opening 17 shown in FIGS. 1-4 is polygonal (e.g., substantially rectangular) in shape and there is but a single opening 17, as shown in FIG. 9, in an alternate embodiment, the distal end 14' may include a plurality of (e.g., two) smaller-dimensioned openings 17a, 17b formed therein to provide access to the plenum space 15. Advantageously, smaller-dimensioned openings 17a, 17b suck in a smaller amount of the subject's skin 60 during blood draw; hence, their use results in less subject discomfort. Although the shape of the openings 17a, 17b in FIG. 9 is circular, that is done for illustrative purposes only. Those of ordinary skill in the art can appreciate that any logical shape may be used to provide a conduit between the puncture points 64a, 64b in the subject's epidermis 60 and the plenum space 15.

In some variations, a blood diverter 91 may be formed between the openings 17a, 17b, such that the blood diverter 91 is capable of directing the flow of blood originating at the first opening 17a around the second opening 17b. Preferably, to avoid microfluidic flow conditions, there is sufficient clearance (e.g., 2-3 mm) 92 between the blood diverter 91 and a sidewall 93 formed about the openings 17a, 17b.

A one-way valve 18 may be formed on a first portion of the housing 12 of the suction cup 11, while a connection 19 for connecting a blood sample container 40 to the suction cup 11 may be formed on a second portion of the housing 12. In some embodiments, the one-way valve 18 and the connection 19 are disposed on opposing sides of the housing 12 of the suction cup 11.

In some variations, the connection 19 is structured and arranged to releasably couple a blood sample container 40 to the housing 12 of the suction cup 11 for the purpose of collecting capillary blood. For example, in some implementations, the connection 19 may include a (e.g., circular) connection opening 21 formed through the housing 12. In some variations, the lumen of the blood sample container 40 passes through the connection opening 21, such that, during use, the opening 45 in the blood sample container 40 may be held at a pressure that is less than atmospheric pressure. Preferably, the (e.g., circular) connection opening 21 may be dimensioned to be slightly greater that the largest outer dimension (e.g., diameter) of the opening 45 of the blood sample container 40. A sealing device(s) 22 may be operatively disposed about the connection opening 21. In some variations, the sealing device 22 may be an (e.g., plastic, elastomer, rubber, silicone, and so forth) O-ring. The sealing device 22 may be a separate item or may be integrated into the connection 19 and the housing 12 of the suction cup 11. One or more collection container locks or clips 23 may be disposed about the connection opening 21 that are structured and arranged so as to (e.g., tightly) compress the sealing device 22 between the connection opening 21 in the housing 12 of the suction cup 11 and the blood sample container 40.

Referring to FIGS. 5A and 5B, a device for transporting or channeling blood from the sampling point into the lumen of a blood sample container 40 without using spontaneous capillary flow will be described. In some embodiments, the transporting or channeling device may include a slide 50 and sidewall elements 55 and may be formed between the opening 17 of the housing 12 of the suction cup 11 and the connection opening 21 of the connection 19. The slide 50 may be manufactured of rigid plastic, an elastomer, and the like. In some variations, a hydrophobic agent may be applied to the slide 50 to better repel the blood, making it slide more easily down the slide 50 toward the blood sample container 40.

Although the shape of the slide 50 will be described as being highly rounded or concave, that is done for illustrative purposes only. Those of ordinary skill in the art can appreciate that, in addition to being concave, the shape of the slide 50 can be rectangular, rounded rectangular, and so forth. In some applications, a first end of the (e.g., concave) slide 50 is cantilevered (e.g., at an obtuse angle) from the housing 12 of the suction cup 11 near the opening 17 of the housing 12, while the second, opposing end is a free end under which a blood sample container 40 may be placed. Advantageously, the (e.g., concave) slide 50 may be structured and arranged to provide gravity-fed, open channel flow to transport or channel blood down and away from the sampling point and the opening 17 in the housing 12 of the suction cup 11. In some variations, the sidewall elements 55 are structured and arranged to channel or funnel blood (e.g., using gravity) from the sampling point into cantilevered end of the (e.g., concave) slide 50. Advantageously, the (e.g., concave) slide 50 is sufficient wide so that it does not transport or channel blood via spontaneous capillary flow, relying, instead on gravity and the hydrophobic nature of the surface of the (e.g., concave) slide 50. Slide widths in excess of 1 mm may be used to avoid open, microfluidic conditions. For example, the width of the slide 50 may be between about 3 mm and about 5 mm; although, widths in excess of 5 mm or less than 3 mm may be used.

In some implementations, the sidewall elements 55 may be formed about the opening 17 of the housing 12 of the suction cup 11 for the purpose of channeling or funneling blood towards the (e.g., concave) slide 50 and the blood sample container 40. For example, in some variations, the sidewall elements 55 may be formed at the same end of the housing 12 of the suction cup 11 as the connection 19. The (e.g., concave) slide 50 may be formed on the housing 12 of the suction cup 11 within the plenum space 15, fixedly attached, at a first, proximal end, to the sidewall elements 55. The second, distal end of the (e.g., concave) slide 50 may be structured and arranged to hang freely over the opening 45 of any blood sample container 40 connected to the connection 19 to the housing 12 of the suction cup 11.

The second, mid-body subassembly 20 may consist or consist essentially of a (e.g., elongate, rectangular or rounded rectangular) housing 29 that is formed to provide an open, proximal end 24; an open, distal end 25; and a plenum space 26 therebetween. Preferably, the outer, peripheral dimensions of the second, mid-body subassembly 20 are configured to provide a tight interference fit between the outer, peripheral surfaces of the (e.g., elongate, rectangular or rounded rectangular) housing 29 and the corresponding inner surfaces of the suction cup 11 of the collection cup subassembly 10. Optionally, the outer, peripheral dimensions of the second, mid-body subassembly 20 may be fixedly attached (e.g., using an adhesive, plastic welding, and the like) to the corresponding inner surfaces of the housing 12 of the suction cup 10 of the collection cup subassembly 10. Although the mid-body subassembly 20 is described as a separate element of the device 100, those of ordinary skill in the art can appreciate that, in some implementations, the collection cup subassembly 10 and the mid-body subassembly 20 could be manufactured of unitary or monolithic construction.

A pair of tabs or projections 27 may be formed proximate the open, distal end 25 of the mid-body subassembly 20, such that the tabs or projections 27 extend from opposing ends of the (e.g., elongate, rectangular or rounded rectangular) housing 29. A (e.g., cylindrical) protrusion 28 may be formed on each tab or projection 27, for example, to accommodate and retain a biasing element(s) 38 (e.g., a pair of springs). The tabs or projections 27 may be configured to provide a resisting force when the biasing element(s) 38 of the plunger assembly 30 is forced or compressed into the tabs or projections 27.

A lock or tab 37 for preventing the plunger assembly 30 from coming out of the plenum space 26 of the mid-body subassembly 20 may be formed on the housing 29 at the open, proximal end 24. Although FIG. 1 shows a lock or tab 37 that includes projections formed on opposing ends of the (e.g., elongate, rectangular or rounded rectangular) housing 29, this is done for the purpose of illustration rather than limitation. Those of ordinary skill in the art understand that the invention may include any sort of lock or tab 37 that permits the plunger assembly 30 to slidingly translate along the inside surface of the housing 29 of the mid-body subassembly 20; but that prevents the plunger assembly 30, after being inserted into the plenum space 26 of the housing 29 of the mid-body subassembly 20, from coming out of the plenum space 26 of the housing 29 of the mid-body subassembly 20.

The plunger subassembly 30 may consist or consist essentially of a (e.g., elongate, rectangular or rounded rectangular) housing 31 that, at a first, proximal end, is fixedly attached to a (e.g., elongate) pressure plate or base portion 32 and, at a second, distal end, is fixedly attached to a plunger 33. Preferably, the outer dimensions of the plunger 33 are dimensioned to be slightly less than each of the corresponding inner dimensions of the open, proximal end 24 of the mid-body subassembly 20. One or more sealing devices 34 may be operatively disposed about the outer periphery of the plunger 33, such that, when the plunger 33 is inserted into the open, proximal end 24 of the housing 29 of the mid-body subassembly 20, the sealing device 34 creates an airtight seal between the plunger 33 and the open, proximal end 24 of the housing 29 of the mid-body subassembly 20. In some variations, the sealing device 34 may be an (e.g., plastic, elastomer, rubber, silicone, and so forth) O-ring.

In some implementations, a pair of (e.g., cylindrical) protrusions 39 may be formed on opposing ends of the (e.g., elongate) pressure plate or base portion 32 for example, to accommodate and retain a biasing element 38 (e.g., a pair of springs). Each protrusion 39 on the (e.g., elongate) pressure plate or base portion 32 is configured to accommodate a first end of the biasing elements 38, while each protrusion 28 formed on the tabs 27 of the mid-body subassembly 20 is configured to accommodate an opposing, second end of the biasing elements 38.

In some variations, the plunger 33 includes an (e.g., planar) upper surface 35 on which one or more lancet elements 36 are formed. Lancet elements 36 are commercially available and may be pressure activated, such that when an end of the lancet element 36 contacts the epidermis, a needle disposed within the lancet element 36 is, initially, propelled into the epidermis and then retracted. Although the device 100 in the figures includes two lancet elements 36 on the upper surface 35, this is done for illustrative purposes only. Those of ordinary skill in the art can include a single lancet element 36 or more than two lancet elements 36.

Figure 8:
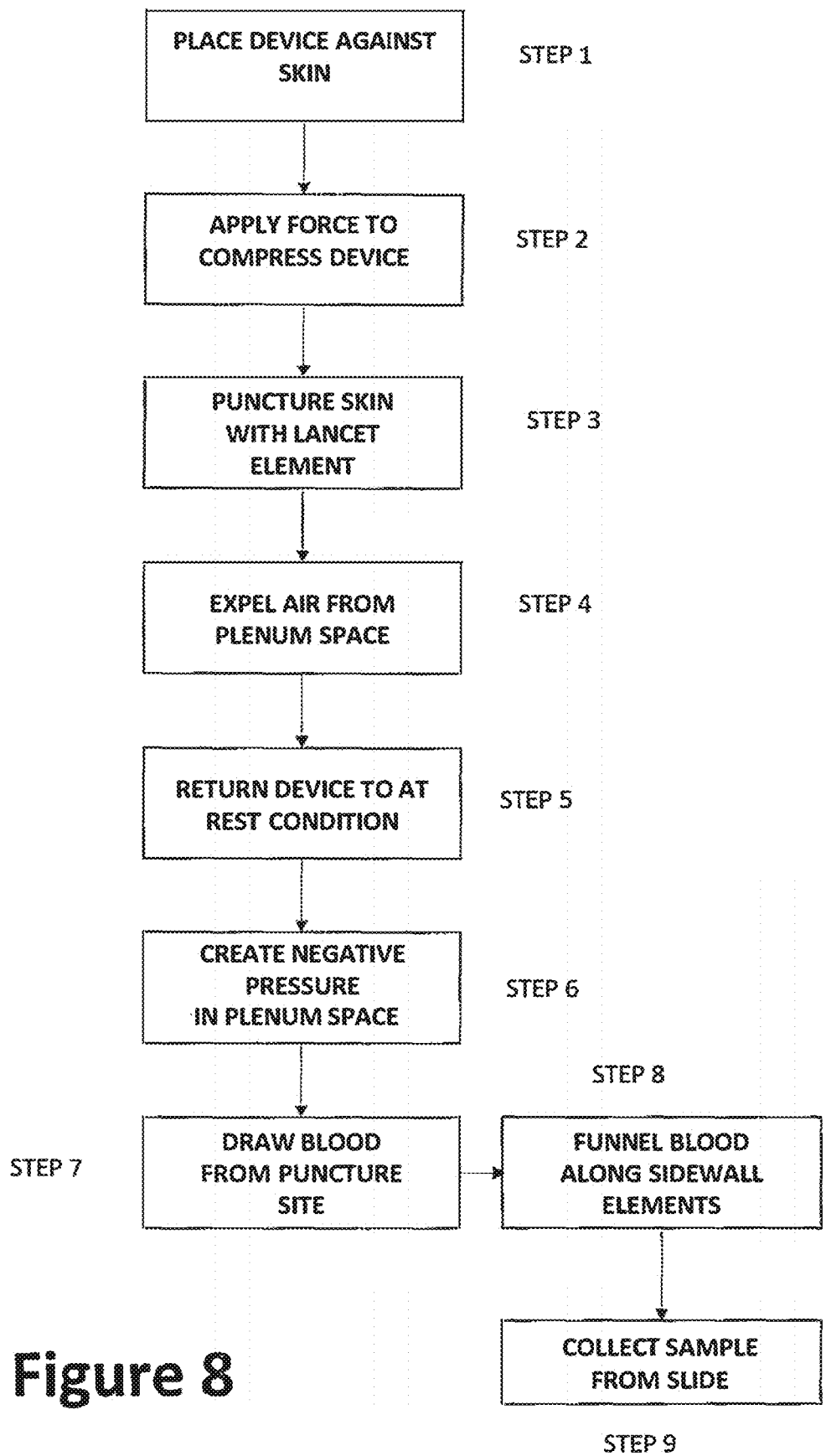
FIG. 8 shows a flow chart of a method of collecting a capillary blood sample, in accordance with some embodiments of the present invention.

Having described a device 100 for collecting blood samples, a method for collecting blood samples in a blood sample container 40 using the device 100 will be described using FIGS. 6-8. FIGS. 1, 2, and 4 show an illustrative embodiment of an uncompressed or at-rest device 100. In a first step, the user places the upper surface 16 of the collection cup subassembly 10 against the skin 60 (e.g., on an upper arm) of the subject (STEP 1). The uncompressed or at-rest device 100 may be characterized as the collection cup subassembly 10 and mid-body subassembly being in a tight interference fit and the plunger assembly subassembly 30 disposed within the plenum spaces 15, 26 of the collection cup subassembly 10 and mid-body subassembly such that the sealing device(s) 34 on the plunger 33 of the plunger subassembly 30 forms an airtight seal with the mid-body subassembly 20 and collection cup assembly 10. Biasing devices 38 (e.g., springs) may be retained, for example, about protrusions 28 on the tabs or projections 27 on the mid-body subassembly 20 and protrusions 39 on the pressure plate or base portion 32 of the plunger subassembly 30.

The user may then force the pressure plate or base portion 32 of the plunger subassembly 30 towards the tabs or projections 27 on the mid-body subassembly 20 and the blood sampling site, so as to compress the biasing device 38 (STEP 2). As shown in FIG. 6, forcing the pressure plate or base portion 32 of the plunger subassembly 30 towards the tabs or projections 27 on the mid-body subassembly 20 causes the lancet elements 36 to advance towards and puncture the epidermis 60 at the blood sampling site (STEP 3). Forcing the pressure plate or base portion 32 of the plunger subassembly 30 towards the tabs or projections 27 on the mid-body subassembly 20 also compresses and, subsequently, expels air contained within the plenum spaces 15, 26 of the collection cup subassembly 10 and mid-body subassembly 20 out of the plenum spaces 15, 26 via the one-way valve 18 (STEP 4).

Once the lancet elements 36 have punctured the subject's skin 60, the user may then remove the force from the pressure plate or base portion 32 of the plunger subassembly 30, which causes the compressed biasing device 38 to return the device 100 to its uncompressed or at-rest state while the upper surface 16 of the collection cup subassembly 10 remains in contact with and pressed against the subject's epidermis 60 (STEP 5). In some application, an adhesive may be placed on the upper surface 16 of the housing 12 of the collection cup subassembly 10 to improve the seal. Advantageously, the lock or tab 37 on the housing 29 of the mid-body assembly 20 prevents the plunger 33 of the plunger subassembly 30 from retracting from the plenum space 26 of the mid-body subassembly 20. As the biasing device 38 causes the plunger subassembly 30 return to its uncompressed or at-rest state, a negative pressure (i.e., a pressure less than atmospheric or ambient pressure) may be created within the plenum spaces 15, 26 of the collection cup subassembly 10 and mid-body subassembly 20 (STEP 6). As shown in FIG. 7, the negative pressure created in the plenum spaces 15, 26 draws the subject's epidermis 60 into the plenum space 15 via the opening 17 in the housing 12 of the collection cup subassembly 10, creating a bulge 62 in the epidermis 60. Advantageously, the negative pressure further encourages blood 65 to leave the body through the one or more puncture points or openings 64 created by the lancet elements 36 (STEP 7).

As shown in FIG. 7, the device 100 is structured and arrange so that gravity—rather than spontaneous capillary flow—will cause the blood 65 to flow down the subject's epidermis 60 towards the sidewall elements 55. Once sufficient blood 65 pools on the sidewall elements 55, the sidewall elements 55 will channel or funnel the pooled blood 65 towards the fixed end of the cantilevered (e.g., concave) slide 50 (STEP 8). The blood 65 may then travel down the (e.g., concave) slide 50 towards its free end that is disposed above the opening 45 of a blood sample container 40. Once the blood reached the free end of the (e.g., concave) slide 50, the blood 65 may fall into the lumen of the blood sample container 40 (STEP 9).

Once sufficient blood has been collected in the blood sample container 40, the user may remove the device 100 from against the subject's epidermis 60 and staunch the further flow of blood 65.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

What is claimed is:

1. A device for collecting blood from a mammalian subject without using spontaneous capillary blood flow, the device comprising:
   a collection cup subassembly comprising:
      a housing; and
      a cantilevered slide structured and arranged in the housing for transporting blood down and away from a blood sampling location; and
   a mid-body subassembly couplable to the collection cup subassembly and comprising:
      a housing having a proximal end and a distal end and defining a plenum space; and
      a tab formed at the proximal end of the housing for retaining a plunger subassembly within the plenum space.

2. The device of claim 1, wherein the slide is cantilevered at an obtuse angle from an opening in the housing in the collection cup subassembly.

3. The device of claim 1, wherein the slide has a shape is selected from the group consisting of a concave slide, a rectangular slide, a rounded rectangular slide, or a V-shaped slide.

4. The device of claim 1, wherein a hydrophobic agent is applied to the slide.

5. The device of claim 1, wherein the collection cup subassembly further comprises a plurality of sidewall elements that are formed within and about at least one opening in the housing and that are structured and arranged to funnel blood from the blood sampling location to the slide.

6. The device of claim 1, wherein the collection cup subassembly further comprises a one-way valve disposed in the housing for creating a negative pressure within a plenum space within the housing.

7. The device of claim 1, wherein the housing of the collection cup subassembly comprises a connection opening structured and arranged for releasably connecting a blood sample container to the housing of the collection cup subassembly.

8. The device of claim 1, wherein the housing comprises at least one opening formed therethrough for placement against the epidermis of the subject.

9. The device of claim 8, wherein the at least one opening comprises a plurality of openings.

10. The device of claim 9 further comprising a blood diverter configured to divert blood flow originating from a first opening around a second opening.

11. The device of claim 10, wherein blood flow is diverted along a path that exceeds 2 mm.

12. The device of claim 1, wherein the mid-body subassembly further comprises a pair of opposing tabs formed at the distal end of the housing, wherein the opposing tabs are configured to retain at least one biasing element.

13. The device of claim 12, wherein the biasing element comprises a pair of springs.

14. The device of claim 1, wherein
the plunger subassembly includes a first end and a second end and comprises:
a plunger formed at the second end; and
at least one lancet elements attached to the plunger.

15. The device of claim 14, wherein the plunger and lancet elements are structured and arranged to translate through the collection cup subassembly to the blood sampling location.

16. The device of claim 14, wherein the plunger subassembly further comprises a base portion formed at the first end.

17. The device of claim 16, wherein the base portion comprises a pair of protrusions that are structured and arranged to retain a biasing element.

18. The device of claim 14, wherein the plunger is structured and arranged to create a negative pressure within the collection cup subassembly.

19. The device of claim 14, wherein the plunger subassembly further comprises at least one sealing device disposed about the plunger.

20. A method for collecting blood from a mammalian subject without using spontaneous capillary blood flow, the method comprising:
providing a blood collecting device comprising:
a collection cup subassembly comprising a cantilevered slide for transporting blood down and away from a blood sampling location;
a mid-body subassembly couplable to the collection cup assembly and comprising:
a housing having a proximal end and a distal end and defining a plenum space and
a tab formed at the proximal end of the housing for retaining a plunger subassembly within the plenum space; and
the plunger subassembly having a first end and a second end and comprising:
a plunger formed at the second end; and
at least one lancet elements attached to the plunger;
placing the device at a blood sampling point;
applying a force to compress a biasing device, such that the plunger and lancet elements advance towards the blood sampling location;
funneling blood down and away from the blood sampling location towards the slide; and
collecting blood traveling by a gravity feed via the slide in a blood sample container disposed through an opening in the housing of the collection cup subassembly.

21. The method of claim 20, wherein the slide is cantilevered at an obtuse angle from the opening in the housing in the collection cup subassembly.

22. The method of claim 20, wherein compressing the biasing device causes air within the device to be expelled, creating a negative pressure within the device.

23. The method of claim 22, wherein the negative pressure is created by expelling air via a one-way valve.

24. A device for collecting blood from a mammalian subject without using spontaneous capillary blood flow, the device comprising:
a collection cup subassembly comprising:
a housing comprising a plurality of openings formed therethrough for placement against the epidermis of the mammalian subject; and
a cantilevered slide structured and arranged in the housing for transporting blood down and away from a blood sampling location; and
a mid-body subassembly couplable to the collection cup assembly and comprising:
a housing having a proximal end and a distal end and defining a plenum space and
a pair of opposing tabs formed at the distal end of the housing, wherein the opposing tabs are configured to retain at least one biasing element.

25. The device of claim 24, wherein the biasing element comprises a pair of springs.

26. A device for collecting blood from a mammalian subject without using spontaneous capillary blood flow, the device comprising:
a collection cup subassembly comprising:
a housing and
a cantilevered slide structured and arranged in the housing for transporting blood down and away from a blood sampling location;
a plunger subassembly having a first end and a second end and comprising:
a plunger formed at the second end;
at least one lancet elements attached to the plunger; and
a base portion formed at the first end and comprising a pair of protrusions that are structured and arranged to retain a biasing element.

* * * * *